United States Patent [19]

Tran

[11] Patent Number: 5,744,470
[45] Date of Patent: Apr. 28, 1998

[54] METHOD FOR TREATING INSOMNIA

[75] Inventor: Pierre Van Tran, Carmel, Ind.

[73] Assignee: Eli Lilly and Company, Indianapolis, Ind.

[21] Appl. No.: 799,052

[22] Filed: Feb. 10, 1997

Related U.S. Application Data

[60] Provisional application No. 60/013,126 Mar. 11, 1996.

[51] Int. Cl.$^6$ .................................................. A61K 31/55
[52] U.S. Cl. ............................................................ 514/220
[58] Field of Search ................................................ 514/220

[56] References Cited

U.S. PATENT DOCUMENTS

| | | | |
|---|---|---|---|
| 5,229,382 | 7/1993 | Chakrabarti et al. | 514/220 |
| 5,631,250 | 5/1997 | Bunnell et al. | 514/220 |

*Primary Examiner*—Raymond Henley, III
*Attorney, Agent, or Firm*—Arleen Palmberg; MaCharri Vorndran-Jones; David E. Boone

[57] ABSTRACT

The invention provides a method for treating insomnia comprising administering an effective amount of olanzapine to a patient in need thereof.

11 Claims, No Drawings

METHOD FOR TREATING INSOMNIA

FIELD OF THE INVENTION

This application claims the benefit of U.S. Provisional Application No. 60/013,126, filed Mar. 11, 1996.

This invention provides a method for using 2-methyl-4-(4-methyl-1-piperazinyl)-10H-thieno[2,3-b][1,5]benzodiazepine, (hereinafter referred as "olanzapine"), for the treatment of insomnia.

BACKGROUND OF THE INVENTION

Insomnia is one of the most common complaints in general medical practice. There is a one year prevalance of as high as 40%. DSM-IV, p. 553 (American Psychiatric Association, Washington, D.C. 1994). A variety of pharmacological agents are used to treat insomnia; however, the "perfect" agent would allow sleep to occur, with normal sleep architecture, rather than produce a pharmacologically altered sleep pattern. The "perfect" agent would not cause next-day effects, either rebound anxiety or continued sedation. There continues to be a need for more desirable drugs having at least several of the characteristics described for the "perfect" agent.

Benzodiazepine hypnotics have been prescribed in the past; however, benzodiazepines are generally not a drug of choice for the treatment of insomnia due to benzodiazepine side effects and difficulties with treating the elderly patient with benzodiazepines. Untreated or improperly treated insomnia is associated with a four fold increase in accidents. Goodman and Gillman, *The Pharmacological Basis of Therapeutics*, 385 (McGraw Hill, New York 9th ed.) 1996.

Thus, there is a need for additional pharmacological treatments for the patient suffering from insomnia. Such pharmacological treatment should most preferredly provide a safety profile which is acceptable for long-term use, if necessary or desired.

It is known that olanzapine can provide antipsychotic activity and is currently undergoing investigation for this purpose. Olanzapine is a known compound and described in U.S. Pat. No. 5,229,382 as being useful for the treatment of schizophrenia, schizophreniform disorder, acute mania, mild anxiety states, and psychosis. U.S. Pat. No. 5,229,382 is herein incorporated by reference in its entirety. However, olanzapine was not known to be useful for the treatment of insomnia. Applicants have discovered that olanzapine can be useful for the treatment of insomnia. Olanzapine could address a long felt need for treatments which provides a favorable safety profile and effectively provides relief for the patient suffering from insomnia.

SUMMARY OF THE INVENTION

The presently claimed invention provides a method for treating insomnia, comprising administering an effective amount of olanzapine or a pharmaceutically acceptable salt thereof to a patient in need of such treatment.

A preferred embodiment of the present invention is treating insomnia in a patient selected from the group consisting of an elderly patient, a patient suffering from long term insomnia, and in a patient who has been taking a hypnotic agent for more than three consecutive weeks.

A further preferred embodiment is a method for treating insomnia without clinically significant alteration of the sleep architecture, comprising administering an effective amount of olanzapine or a pharmaceutically acceptable salt thereof to a patient in need of such treatment.

DETAILED DESCRIPTION OF THE INVENTION

Olanzapine is of the formula

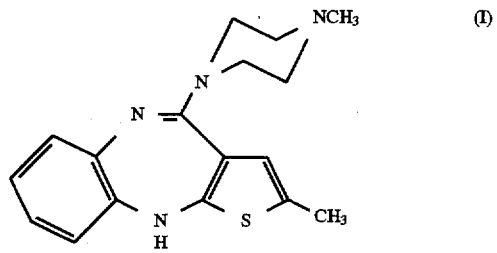

or an acid addition salt thereof.

As used herein the phrase "clinically significant alteration of the sleep architecture" means that the patient suffering from insomnia is able to sleep without a clinically significant pharmacological alteration of the sleep pattern. Most preferably, the patient additionally suffers no "rebound effect" from the treatment. The term "rebound effect" refers to manifestations such as anxiety upon waking.

It is especially preferred that olanzapine will be the Form II olanzapine polymorph having a typical x-ray powder diffraction pattern as represented by the following interplanar spacings:

| d |
|---|
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007 |

A typical example of an x-ray diffraction pattern for Form II is as follows wherein d represents the interplanar spacing and $I/I_1$ represents the typical relative intensities:

| d | $I/I_1$ |
|---|---|
| 10.2689 | 100.00 |
| 8.577 | 7.96 |
| 7.4721 | 1.41 |
| 7.125 | 6.50 |

-continued

| d | I/I₁ |
|---|---|
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

The x-ray diffraction patterns set out herein were obtained using a Siemens D5000 x-ray powder diffractometer having a copper $K_\alpha$ radiation source of wavelength, $\lambda=1.541Å$.

It is further preferred that the Form II olanzapine polymorph will be administered as the substantially pure Form II olanzapine polymorph. As used herein "substantially pure" refers to Form II associated with less than about 5% Form I, preferably less than about 2% Form I, and more preferably less than about 1% Form I. Further, "substantially pure" Form II will contain less than about 0.5% related substances, wherein "related substances" refers to undesired chemical impurities or residual solvent or water. In particular, "substantially pure" Form II should contain less than about 0.05% content of acetonitrile, more preferably, less than about 0.005% content of acetonitrile. Additionally, the Form II polymorph preferably contains less than 0.5% of associated water.

The polymorph obtainable by the process taught in the '382 patent will be designated as Form I and has a typical x-ray powder diffraction pattern substantially as follows, obtained using a Siemens D5000 x-ray powder diffractometer, wherein d represents the interplanar spacing:

| d |
|---|
| 9.9463 |
| 8.5579 |
| 8.2445 |
| 6.8862 |
| 6.3787 |
| 6.2439 |
| 5.5895 |
| 5.3055 |
| 4.9815 |
| 4.8333 |
| 4.7255 |
| 4.6286 |
| 4.533 |
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |
| 2.948 |
| 2.8172 |
| 2.7589 |
| 2.6597 |
| 2.6336 |
| 2.5956 |

A typical example of an x-ray diffraction pattern for Form I is as follows wherein d represents the interplanar spacing and I/I₁ represents the typical relative intensities:

| d | I/I₁ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns herein were obtained with a copper $K_{60}$ of wavelength $\lambda=1.541Å$. The interplanar spacings in the column marked "d" are in Angstroms. The typical relative intensities are in the column marked "I/I₁".

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

As used herein, the term "insomnia" shall refer to a condition characterized by the inability of an individual to fall asleep or to maintain sleep for the desired amount of time necessary to provide a rested, alert feeling upon waking. To further clarify, the term insomnia shall refer to the condition classified in the DSM-IV, p. 553 (American Psychiatric Association, Washington, D.C. 1994) as Catagory number 307.42. Diagnostic criteria include a predominant complaint in difficulty initiating or maintaining sleep, or nonrestorative sleep, for at least one month; The sleep disturbance causes clinically significant distress or impairment of social, occupational, or other important areas of functioning; The sleep disturbance does not occur exclusively during the course of Narcolepsy, Breathing related sleep disorder, circadian rhythm sleep disorder, or a parasomna; The disturbance does not occur exclusively during the course of a mental disorder; The disturbance is not due to the physiological effects of a substance or a general medical condition.

The results of pharmacological studies show that olanzapine has muscarinic cholinergic receptor activity. The compound is active at the dopamine D-1 and D-2 receptors as indicated by an IC50 of less than 1 µM in the 3H-SCH233390 (Billard, et al. Life Sciences 35:1885 (1984)) and the 3H spiperone (Seeman et al Nature 216:717 (1976)) binding assays respectively. Further, olanzapine is active at the 5-HT-2 receptor and 5-HT1C receptor. The complex pharmacological profile of the compound provides a medicament which can be useful for the treatment of insomnia.

The usefulness of the compound for treating insomnia can be supported by the following studies as described.
Clinical observations.

A double-blind multicenter clinical trial was designed to assess the safety and efficacy of olanzapine. Patients were randomized to olanzapine or placebo. The results of the study suggest that olanzapine can be useful for the treatment of insomnia.

Olanzapine is effective over a wide dosage range, the actual dose administered being dependent on the condition being treated. For example, in the treatment of adult humans, dosages of from 5 to 25 mg per day may be used. A once a day dosage is normally sufficient. For treatment of insomnia, a dose range of from 5 to 100 mg, is suitable, while a dosage of from 5 to 25 mg per day is preferred. Radiolabelled olanzapine, can be detected in the saliva and thus the compound can potentially be monitored in patients to assess compliance.

A preferred formulation of the invention is a solid oral formulation comprising from about 5 to about 25 mg of olanzapine as an effective amount of the active ingredient.

Most preferably, the solid oral formulation is contained in packaging materials which protect the formulation from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

Olanzapine will normally be administered orally and, for this purpose, it is usually employed in the form of a pharmaceutical composition.

Accordingly, pharmaceutical compositions comprising olanzapine, as active ingredient associated with a pharmaceutically acceptable carrier may be prepared. In making the compositions of the invention conventional techniques for the preparation of pharmaceutical compositions may be used. For example, the active ingredient will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. The active ingredient can be adsorbed on a granular solid container for example in a sachet. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxy-benzoate, talc, magnesium stearate or mineral oil. The compositions of the invention may, if desired, be formulated so as to provide quick, sustained or delayed release of the active ingredient after administration to the patient.

Depending on the method of administration, the compositions for the treatment of central nervous system conditions may be formulated as tablets, capsules, injection solutions for parenteral use, gel or suspension for transdermal delivery, suspensions or elixirs for oral use or suppositories. Preferably the compositions are formulated in a unit dosage form, each dosage containing from usually 5 to 25 mg, of the active ingredient.

The materials for the present invention can be purchased or prepared by a variety of procedures well known to those of ordinary skill in the art. Olanzapine can be prepared as described by Chakrabarti in U.S. Pat. No. 5,229,382 ('382), herein incorporated by reference in its entirety. Further, the following preparations illustrate a method for preparing of the especially preferred Form II olanzapine polymorph.

Compound characterization methods include, for example, x-ray powder pattern analysis, thermogravimetric analysis (TGA), differential scanning calorimetery (DSC), titrametric analysis for water, and $H^1$-NMR analysis for solvent content.

The following examples are provided for purposes of illustration and are not to be construed as limiting the scope of the claimed invention.

PREPARATION 1

Technical Grade olanzapine

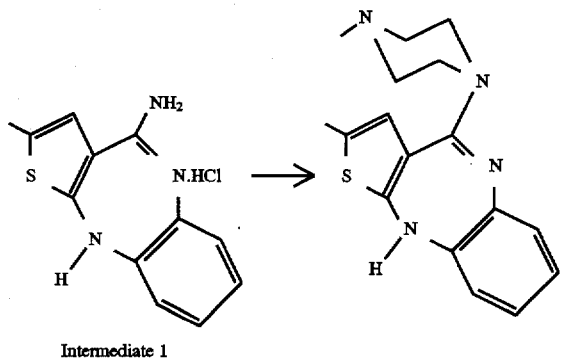

Intermediate 1

In a suitable three neck flask the following was added:
Dimethylsulfoxide (analytical): 6 volumes
Intermediate 1:75 g
N-Methylpiperazine (reagent): 6 equivalents
Intermediate 1 can be prepared using methods known to the skilled artisan. For example, the preparation of the Intermediate 1 is taught in the '382 patent.

A sub-surface nitrogen sparge line was added to remove the ammonia formed during the reaction. The reaction was heated to 120° C. and maintained at that temperature throughout the duration of the reaction. The reactions were followed by HPLC until ≦5% of the intermediate 1 was left unreacted. After the reaction was complete, the mixture was allowed to cool slowly to 20° C. (about 2 hours). The reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical olanzapine.

Yield: 76.7%; Potency: 98.1%

PREPARATION 2

Form II olanzapine polymorph

A 270 g sample of technical grade 2-methyl-4-(4-methyl-1-piperazinyl)-10H-thieno[2,3-b][1,5]benzodiazepine was suspended in anhydrous ethyl acetate (2.7 L) The mixture was heated to 76° C. and maintained at 76° C. for 30 minutes. The mixture was allowed to cool to 25° C. The resulting product was isolated using vacuum filtration. The product was identified as Form II using x-ray powder analysis.

Yield: 197 g.

The process described above for preparing Form II provides a pharmaceutically elegant product having potency ≧97%, total related substances <0.5% and an isolated yield of >73%.

EXAMPLE 1

A portion of the hydroxypropyl cellulose was dissolved in purified water to form a solution for granulation. The remaining hydroxypropyl cellulose (total of 4.0% w/w final tablet weight), which was an extra fine grade, was combined with the olanzapine (1.18% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer. The running powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating:

Hydroxypropyl methylcellulose (10% w/w) was mixed with purified water to form a solution. Core tablets were divided into approximately equal sections and spray coated with the hydroxypropyl methylcellulose solution. The operation was performed in a perforated coating pan.

Coating of Core Tablets:

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

We claim:

1. A method for treating insomnia comprising administering to a mammal in need of such treatment, an effective amount olanzapine, or a pharmaceutically acceptable salt thereof.

2. A method of claim 1 wherein olanzapine is Form II olanzapine having a typical x-ray diffraction pattern as follows, wherein d represents the interplanar spacing:

| d |
|---|
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007 |

3. A method of claim 1 wherein the patient in need of treatment is elderly.

4. A method of claim 1 wherein the patient is suffering from long-term insomnia which has occurred for more than three consecutive weeks.

5. A method of claim 1 wherein the patient has been previously treated with a hypnotic agent.

6. A method of claim 1 wherein the effective amount is from about 1 mg to about 25 mg per day.

7. A method of claim 6 wherein the effective amount is from about 5 mg to about 20 mg per day.

8. A method for treating insomnia, wherein the such treatment provides no clinically significant alteration of the sleep architecture, comprising administering an effective amount of olanzapine or a pharmaceutically acceptable salt thereof to a patient in need of such treatment.

9. A method of claim 8 wherein the effective amount is an amount of from about 5 mg to about 25 mg per day.

10. A method of claim 9 wherein the patient is elderly.

11. A method of claim 9 wherein the olanzapine is Form II olanzapine having a typical x-ray diffraction pattern as follows, wherein d represents the interplanar spacing:

| d |
|---|
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |

-continued

| d |
|---|
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007 |

\* \* \* \* \*